United States Patent [19]
Froeberg et al.

[11] Patent Number: 5,378,177
[45] Date of Patent: Jan. 3, 1995

[54] DEVICE FOR AFFIXING AN ELECTRODE CABLE TO AN APPARATUS

[75] Inventors: Paul Froeberg, Bromma; Goeran Johannson, Sollentuna, both of Sweden

[73] Assignee: Siemens-Elema AB, Solna, Sweden

[21] Appl. No.: 161,266

[22] Filed: Dec. 3, 1993

[30] Foreign Application Priority Data

Jan. 12, 1993 [SE] Sweden ............................. 9300059-4

[51] Int. Cl.$^6$ ............................................. H01R 4/52
[52] U.S. Cl. ..................................... 439/836; 439/265; 607/37
[58] Field of Search ................... 607/37; 439/259, 265, 439/345, 346, 816, 835, 836, 725

[56] References Cited

U.S. PATENT DOCUMENTS

| | | | |
|---|---|---|---|
| 3,908,668 | 9/1975 | Bolduc | 128/419 P |
| 4,226,244 | 10/1980 | Coury et al. | 128/419 P |
| 4,784,141 | 11/1988 | Peers-Trevarton | 439/784 X |
| 4,934,367 | 6/1990 | Daglow et al. | 439/527 |

FOREIGN PATENT DOCUMENTS 2347720  4/1974  Germany.

*Primary Examiner*—Khiem Nguyen
*Attorney, Agent, or Firm*—Hill, Steadman & Simpson

[57] ABSTRACT

A device for affixing an electrode cable to an apparatus for emitting electrical pulses, such as a pacemaker or a defibrillator, cooperates with a connector part of the apparatus to which the affixing device for the proximal end of the electrode cable is attached. The electrode cable has a proximal end being provided with a center channel. In order to reduce the size of the connector part of the apparatus while still achieving good fixing of the electrode cable, affixing device includes an elongate body onto which the proximal end of the electrode cable can be mounted and an expander element for radially expanding at least a part of the elongate body, so the body can, when the cable end has been mounted, be affixed by pressure to the surrounding channel wall.

10 Claims, 2 Drawing Sheets

DEVICE FOR AFFIXING AN ELECTRODE CABLE TO AN APPARATUS

BACKGROUND OF THE INVENTION

1. Field of the Invention

The present invention relates to a device for affixing an electrode cable to an apparatus for emitting electrical pulses, such as a pacemaker or a defibrillator, the apparatus being of the type having a connector part to which the affixing device for 10 the proximal end of the electrode cable is attached, and the electrode cable's proximal end having a center channel.

2. Description of the Prior Art

An affixing device of the above-described kind is described in German OS 2 518 571 which is intended for connection of at least one pacemaker electrode to a pacemaker. The affixing device consists of a screw, arranged perpendicularly to the longitudinal axis of the electrode cable, which is screwed into the connector part from the top, affixing the electrode cable's distal end at one point. To prevent the entry of body fluids into the connector part, the opening for the screw is provided with a sealing plug. The use of a screw and the sealing plug makes the connector part relatively tall, an undesirable feature when the aim is to achieve the smallest possible pacemaker dimensions.

Another affixing device for a pacemaker electrode is known from German OS 2 914 034 whose construction is similar to the affixing device described in German OS 2 518 571, although with the difference that the affixing screw and sealing plug in this embodiment are devised to attach and seal the electrode cable respectively from one long side of the connector part, making the connector part relatively thick.

In U.S. Pat. No. 4,934,367, a connector part for a pacemaker is disclosed which has a hollow part partially enclosing the distal end of the electrode cable 35 when the end is attached to the connector part. The affixing means for the electrode end consists of suture thread which the implanting physician knots around the hollow part, a procedure which can be intricate. In addition, this type of affixing is not wholly reliable.

SUMMARY OF THE INVENTION

An object of the present invention is to provide an affixing device of the above-described general kind, but with a reduction in the size of the connector part of the apparatus while simultaneously attaining good fixing of the electrode cable.

The above object is achieved in accordance with the principles of the present invention in an affixing device containing an elongate body onto which the proximal end of the electrode cable can be mounted, and expander means for radially expanding at least a part of the elongate body so the body can, when the cable end has been mounted on it, be affixed by pressure to the surrounding channel wall. Since the elongate body is inserted into the electrode cable's channel and becomes affixed in the channel, the affixing device can be made so small that its external diameter is about equal to the external diameter of the electrode cable's proximal end. In this way, the size of the connector part can be reduced substantially.

According to one constructively simple version of the invention, the elongate body is tubular and provided with at least one longitudinal slot extending along the entire length of the body, the expander means then being slidably arranged in the tube along at least a part of the slot's length.

According to the invention, the expander means is an element whose external diameter is larger than the internal diameter of the section of tube provided with a slot. The expander means should have a shape facilitating its insertion into the tube. A conical or spherical shape is an example of such a shape.

According to one preferred embodiment of the invention, the tube's internal diameter beyond the slotted section is larger than or equal to the external diameter of the expander means. This makes it possible for the expander means to be disposed inside the tube in an non-expanded state, thereby simplifying the mounting of the electrode end.

In a further embodiment of the invention, the elongate body is provided with at least two slots, evenly distributed over the body's surface and running from the body end on which the electrode cable is mounted.

In another embodiment, the body is made of a resilient material. This choice of materials is of very great importance, since the body can resume its original dimensions when the expander means is moved to a position in which the tube is not affected. This makes it possible to detach the electrode end from the body.

In a further embodiment of the invention, the affixing device also includes a holder permanently arranged in the connector part of the apparatus to which the cable is to be affixed, one end of the body being attached to the holder such that the longitudinal axis of the holder is in line with the longitudinal axis of the body. This construction adapts the affixing device to the elongated configuration of the pacemaker and the connector part.

In another embodiment of the invention, the affixing device includes a further holder which can be moved in relation to the aforementioned holder and which is connected to the expander means. This makes it possible to control the expander means in a defined manner.

In another version of the invention the further holder is connected to the expander means by a longitudinally stiff connector element. As a result of the stiff connector element, the expander means can be moved in both directions inside the tube.

The two holders can be advantageously inter-connected by a thread, the further holder than being movable in relation to the first holder when the further holder is rotated, causing the body to expand when the holder is screwed in one direction and to resume its original dimensions when the holder is screwed in the opposite direction.

DESCRIPTION OF THE PREFERRED EMBODIMENTS

Figure 1:
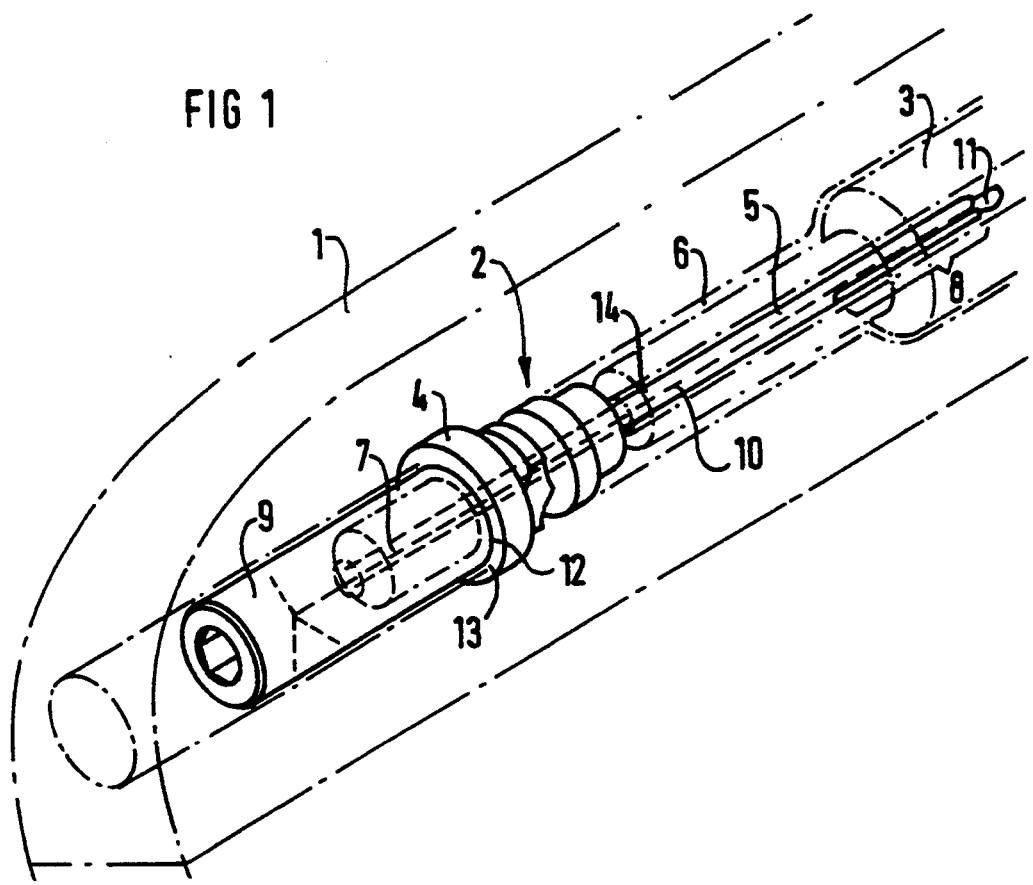
FIGS. 1 and 2 are respective perspective views of an affixing device, constructed in accordance with the principles of the present invention in an expanded and a non-expanded position.
Figure 2:
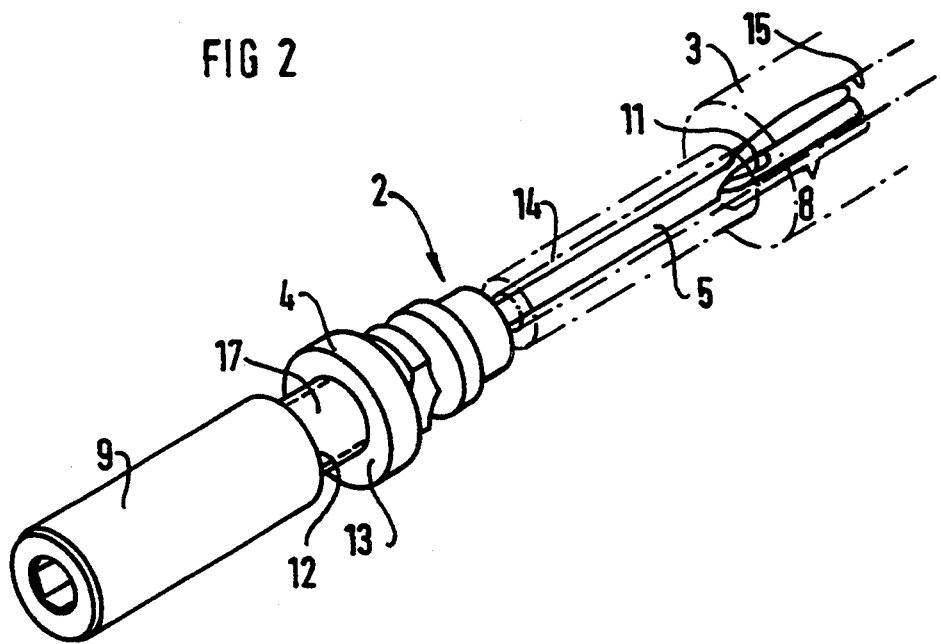

In FIG. 1 shows in dash-dot lines, the contours of a connector part 1 for a pacemaker. An affixing device 2 is arranged in this connector part 1 for affixing the proximal end of an electrode cable 3. The affixing device 2 includes a first holder 4 with an axially extending channel 7 which is permanently arranged in the connector part 1. An elongate, tubular body 5 is attached to the holder 4 such that the longitudinal axis of the holder 4 is in line with longitudinal axis of the elongate body or the tube 5. The tube 5 is, in turn, centrally arranged in an opening 6 in the connector part 1 into which the end of the cable 3 can be introduced. In this embodiment the tube 5 is provided with two slots 8, only one of which can be seen in FIG. 1. The slots 8 extend from the free end of the tube 5 over part of the tube's length. The affixing device also includes an expander element 11, whose external diameter is greater than the internal diameter of the tube 5, which can be introduced into the tube in such a way that it radially expands the part of the tube provided with slots 8. The affixing device 2 also contains a second holder 9 which, by means of a threaded section 17, is movably arranged in relation to the first holder 4 and is connected by a connector element 10 to the expander element 11. The connector element 10, which is longitudinally stiff, runs through the channel of the first holder 4 and through the tube 5. When the second holder 9 is screwed toward the first holder 4 in such a way that the end side 12 of the second holder touches the end side 13 of the first holder 4, the expander element 11 is outside the tube 5. In this position, the cable end 3, which is provided with a centrally arranged channel 14 otherwise intended for a stylet, can be slid onto the tube 5. The second holder 9 can thereafter be rotated with a tool (not shown) so this holder 9 moves in relation to the first holder 4, the expander element 11 also being advanced into the tube 5 between the slots 8 so they expand radially, the tube's inter-slot surface being affixed by pressure to the surrounding channel wall 15, as shown in FIG. 2. When the second holder 9 is rotated so the expander element 11 retracts out of the tube 5, the tube 5 resumes its original shape, since it is made of a resilient material. In this way, the cable end 3 can be detached from the affixing device 2 when a pacemaker is replaced or an electrode cable detached. The expander element 11 should be shaped in a way facilitating its insertion into the slotted section of the tube 5. A conical or spherical shape would be appropriate in this instance.

Figure 3:
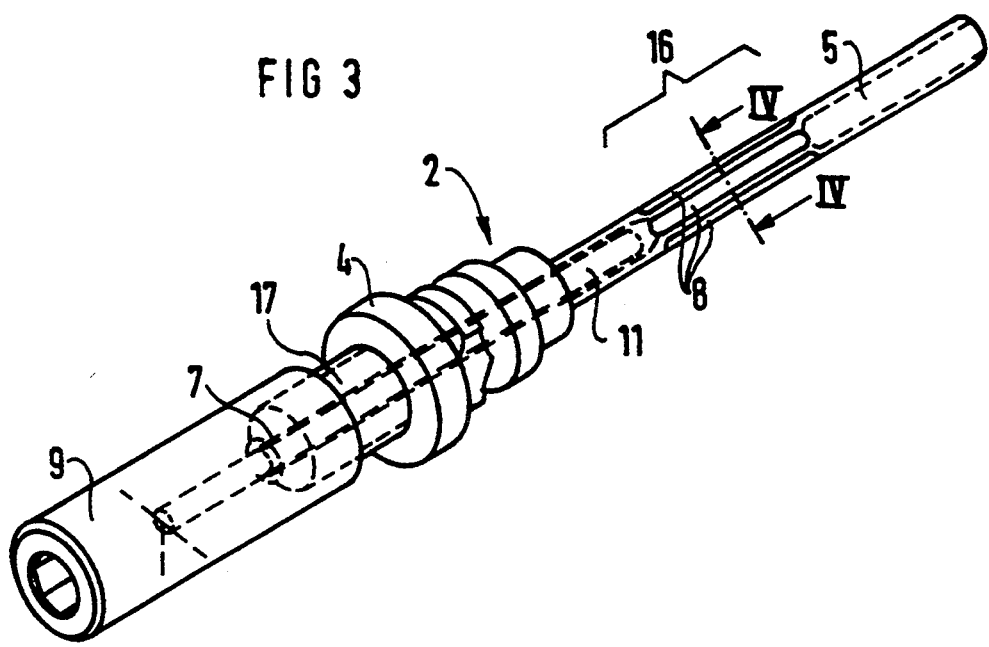
FIG. 3 is a perspective view of a further embodiment of an affixing device, constructed in accordance with the principles of the present invention in a non-expanded position.

In FIG. 3, the slots 8 in the tube 5 of the affixing device 2 are located in about the middle of the tube 5, and the internal of the tube 5 diameter beyond the slotted section 16 is somewhat larger than the external diameter of the expander element 11. This embodiment shows that the expander element 11 can thereby be arranged in the tube 5 even when the tube 5 is not expanded, resulting in a compact affixing device. The FIGS. 3 and 5 also show that screwing in the second holder 9 until the end side 12 of the second holder 9 touches the end side 13 of the first holder 4 causes the expander element 11 to move a corresponding distance inside the tube 5 so at least part of the expander element 11 stops in the slotted section 16, causing that part of the tube 5 to expand. This results in pressure-fixing of the surfaces between the slots 9 to the surrounding channel wall when a cable end has been mounted.

Figure 4:
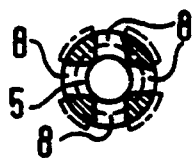
FIG. 4 is a cross-section through the affixing device of FIG. 3 along the section line IV—IV.

In FIG. 4, which is a cross-section through the tube 5 in FIG. 3, the tube 5 is shown in a non-expanded position and in an expanded position. The expanded position is illustrated with the dash-dot contours intended to show the tube section between the slots 9.

Figure 5:
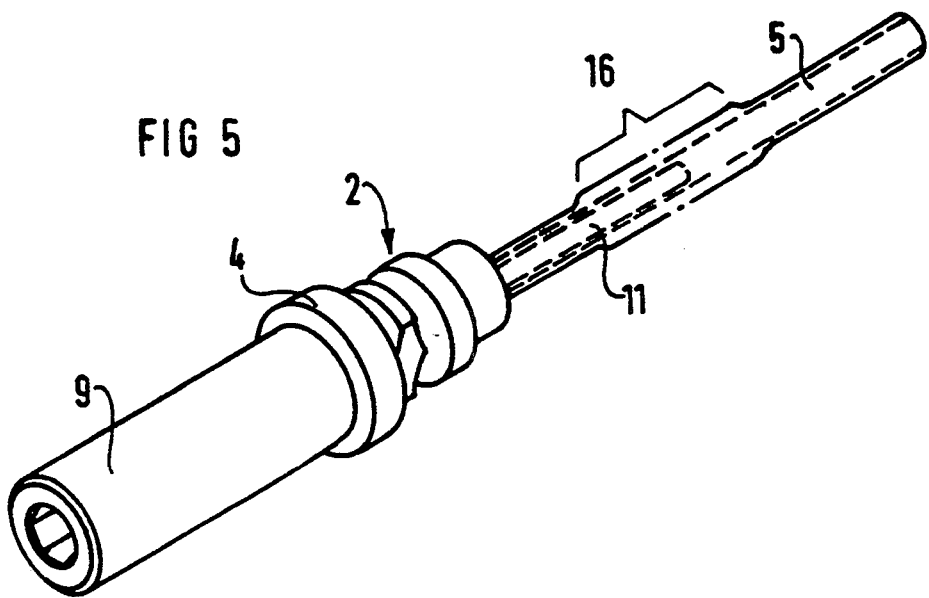
FIG. 5 is a perspective views of the affixing device of FIG. 3 in an expanded position.

In the embodiment shown in FIGS. 3–5, the threads on the first holder 4 can have a convex profile. As a result of this thread profile, the second holder 9 can be advanced against the first holder 4, thereby achieving very rapid looking of the cable end. When the cable end is to be removed from the tube 5, the second holder 9 is screwed back to a position as shown in FIG. 3, and the tube then resumes its original dimensions.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for affixing an electrode cable to an apparatus for emitting electrical pulses, the apparatus having a connector part and the electrode cable having a proximal end with a center channel, said device comprising:
    an elongated body disposed in said connector part onto which said proximal end of said electrode cable can be mounted with said elongated body extending into said channel of said proximal end of said electrode cable; and
    means for radially expanding at least a portion of said elongated body for affixing said elongated body by pressure to a channel wall of said channel.

2. A device as claimed in claim 1 wherein said elongated body is tubular and has a slotted region having at least one longitudinal slot therein, and wherein said means for expanding comprises means for slidably moving in said elongated body along at least a portion of said slotted region.

3. A device as claimed in claim 2 wherein said slotted region has an inner diameter, and wherein said means for expanding comprises an element having an outer diameter which is larger than said inner diameter.

4. A device as claimed in claim 3 wherein said elongated body has a region beyond said slotted region having an inner diameter which is greater than or equal to said outer diameter of said element.

5. A device as claimed in claim 2 wherein said slotted region of said elongated body has at least two slots and wherein said two slots are evenly distributed over a surface of said body and run from an end of said body on which said electrode cable is mounted.

6. A device as claimed in claim 1 wherein said body consists of resilient material.

7. A device as claimed in claim 1 wherein said affixing device further comprises:
    a holder permanently disposed in said connector part, one end of said body being attached to said holder, and said holder having a longitudinal axis aligned with a longitudinal axis of: said body.

8. A device as claimed in claim 7 wherein said affixing device further comprises a further holder movable relative to said holder, and connected to said means for expanding.

9. A device as claimed in claim 8 wherein said further holder is connected to said means for expanding by a longitudinally controllable connector element.

10. A device as claimed in claim 8 wherein said holder and said further holder are connected by a threaded section, said further holder being movable relative to said holder when said further holder is rotated, and said body expanding when said further holder is rotated on said threaded section in one direction and resuming original dimensions when said further holder is rotated on said threaded section in an opposite direction.

* * * * *